Figure 1:
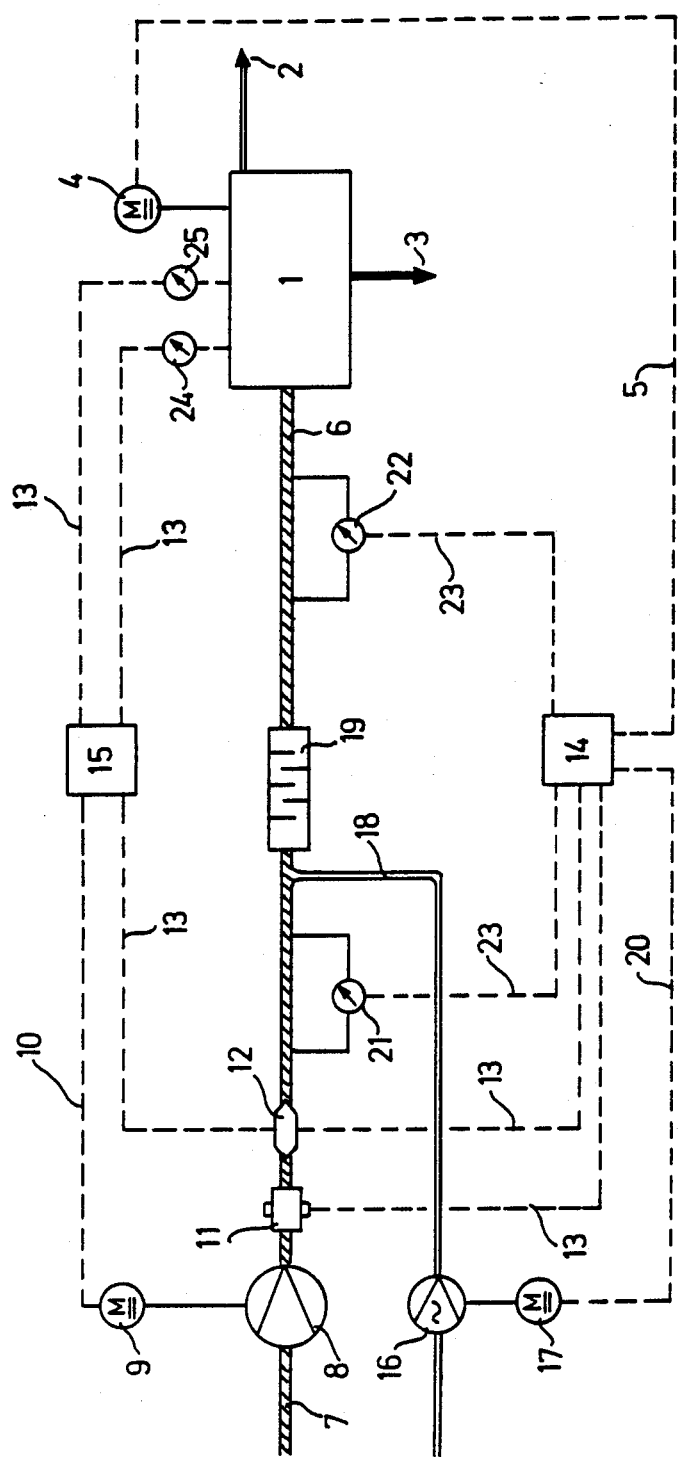

United States Patent [19]

Eisenlauer et al.

[11] Patent Number: 4,576,723
[45] Date of Patent: Mar. 18, 1986

[54] ESTIMATION OF THE DEGREE OF DISPERSION IN FLOWING CONCENTRATED DISPERSIONS

[75] Inventors: Josef Eisenlauer, Ludwigshafen; Dieter Horn, Heidelberg; Manfred Neuwirth, Mannheim, all of Fed. Rep. of Germany

[73] Assignee: BASF Aktiengesellschaft, Fed. Rep. of Germany

[21] Appl. No.: 677,308

[22] Filed: Dec. 3, 1984

[30] Foreign Application Priority Data

Dec. 2, 1983 [DE] Fed. Rep. of Germany ....... 3343598

[51] Int. Cl.[4] .............................................. C02F 1/52
[52] U.S. Cl. .................................... 210/709; 210/745
[58] Field of Search ............... 210/741, 745, 709, 96.1

[56] References Cited

U.S. PATENT DOCUMENTS 3,605,775 9/1971 Zaander et al. ................. 210/745 X
3,812,966 5/1974 Beach et al. ........................ 210/745
4,170,553 10/1979 Lang et al. ...................... 210/745 X
4,282,093 8/1981 Haga et al. ...................... 210/709 X

FOREIGN PATENT DOCUMENTS 3300249 7/1983 Fed. Rep. of Germany .

OTHER PUBLICATIONS

Abwasser 22 5(1980), S282–289.

Primary Examiner—Thomas Wyse
Attorney, Agent, or Firm—Keil & Weinkauf

[57] ABSTRACT

Rapid in situ estimation of the degree of dispersion in flowing two-phase systems, in particular for determining optimum metering of dispersants or flocculants in concentrated dispersions, is carried out by a method in which assignment of the degree of dispersion is effected by measuring the pressure drop experienced by a flowing dispersion along a defined length during tubular flow.

4 Claims, 3 Drawing Figures

ESTIMATION OF THE DEGREE OF DISPERSION IN FLOWING CONCENTRATED DISPERSIONS

The present invention relates to a method for rapid in situ estimation of the degree of dispersion in flowing two-phase systems, in particular for determining the optimum metering of dispersants or flocculants in concentrated dispersions.

It is known that the degree of dispersion can be measured in situ in flowing systems by a laser-optical method, and can be used as a control parameter for optimizing the metering of assistants. Although the laser-optical method avoids some of the problems with soiling of the flow-through cell, which are familiar from simple turbidity measurements, its use is restricted to relatively dilute dispersions which are still transparent. For more highly concentrated dispersions and/or dispersions exhibiting a pronounced tendency to adhesion, a novel ultrasonic system which permits the measurement of particle concentrations in flowing systems has recently become available; however, the sensitivity of this system to changes in the degree of dispersion is not yet clear.

With the aid of a simple turbidity measurement in the form of a submerged probe in the filtrate, attempts have already been made to control sludge dewatering on continuously operating machines via the metering of the flocculant (Korrespondenz Abwasser 27, 5 (1980), 287-289). Furthermore, patent application DE No. 3 300 249 A1 discloses that the mode of operation of dewatering machines can be optimized via the freely flowing amount of filtrate, as a control input of a flocculant control loop. In another prior art method, samples of the flocculated dispersions are taken from the inflow into the dewatering machine, the dewaterability of these samples is determined, and assistants are metered in on the basis of the result.

The disadvantage in these otherwise very useful methods of control is the inertia of the total system. Although the control inputs used are the parameters which are important in practice, e.g. amount of filtrate, dewaterability and turbidity of the filtrate, these are macroscopic secondary effects of the primary flocculation process, and their measurement therefore involves a delay which is as long, or longer, than the residence time in the separation apparatus. In the stated control loops, the amount of assistant is in general initially changed in a random manner. The effects are measured on the basis of secondary parameters, and optimization of the amount of flocculant is continued stepwise. In the case of substantial short-term changes in the dewatering properties of the sludge, difficulties arise in this type of control, since the automatic system cannot, for example, decide whether a change in the amount of filtrate is due to changes in the properties of the sludge or in the amount of assistant added.

It is an object of the present invention, starting from the prior art, to provide a method for the in situ estimation of the degree of dispersion in flowing concentrated dispersions, which reacts rapidly and sensitively to changes in the degree of dispersion and hence provides a reliable control input in an assistant control loop of dispersing or dewatering machines, where the secondary effects induced by the altered degree of dispersion are advantageously utilized.

We have found that this object is achieved, in accordance with the invention, by measurement of the drop in pressure experienced by a flowing dispersion along a defined length of tubular flow, and assignment of the measured value to the degree of dispersion, which can be changed systematically as a function of the metering of the assistant.

According to the invention, the method is particularly advantageously carried out downstream from a point at which an assistant is metered, with the result that metering can be optimized. Furthermore, in the method the result is standardized with the measured value determined, according to the invention, upstream from the point at which the assistant is metered, and the standardized measured value is used as a control input for the assistant control loop in apparatuses for solid/liquid separation, in particular dewatering machines having one or more control loops for adaptation to sludges or dispersions with fluctuating dewatering properties, e.g. a flocculant control loop and/or a throughput control loop or a filter speed control loop (in the case of pressure belt filters).

Rapid in situ measurement of the degree of dispersion in flowing systems can be used for two different purposes. On the one hand, it is possible to monitor the course of dispersion in comminution apparatuses in process engineering. Here, the effect of apparatus-related parameters and dispersants can be investigated. One example is wet comminution with the addition of dispersants. On the other hand, the method is used for measuring the controlled destabilization of dispersions by the addition of flocculants. The primary flocculation process generally results in a change in the macroscopic parameters of the dispersion, e.g. sedimentation or dewatering behavior, this change being used to advantage in solid/liquid separation apparatuses. As a rule, optimum metering of assistants exists for both purposes.

The present method permits the measurements to be carried out in situ, so that very rapid changes in the degree of dispersion as a result of controlled metering of an assistant are detected.

Because of these characteristics, the method appears suitable both for use in laboratory tests for assessing the mode of action of dispersants or flocculants and for on-line monitoring and control of dispersing units or flocculation/dewatering units.

The method is based on the measurement of the pressure drop experienced by a flowing dispersion along a defined length during tubular flow, and the assignment of the measured value to the degree of dispersion, which can be changed by metering dispersants or flocculants. Particularly in the case of concentrated dispersions, the measured effect shows a high degree of correlation with the metering of the assistant, as illustrated in the Examples. The pressure measurement can be carried out using prior art methods.

Figure 2:
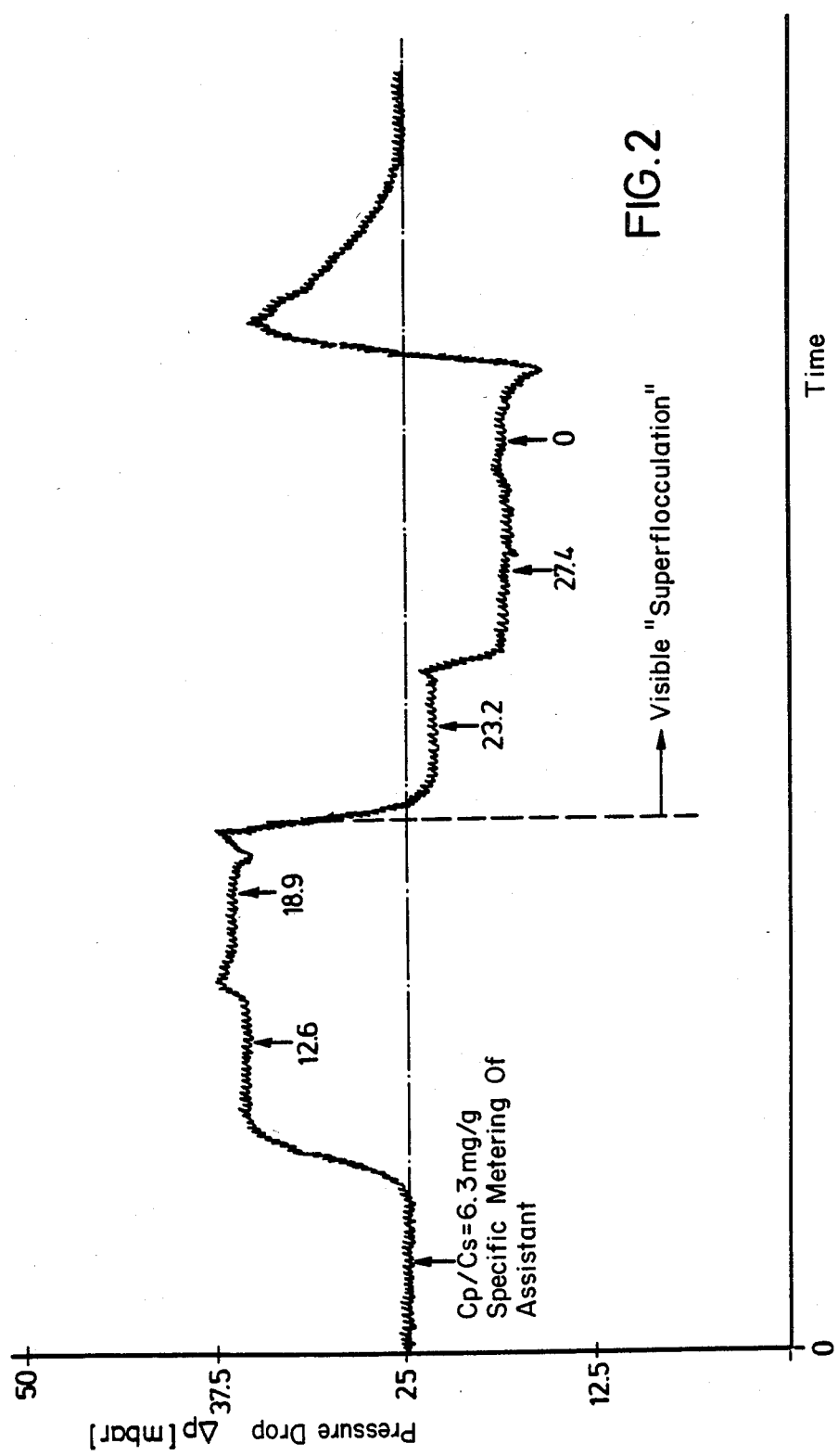
Figure 3:
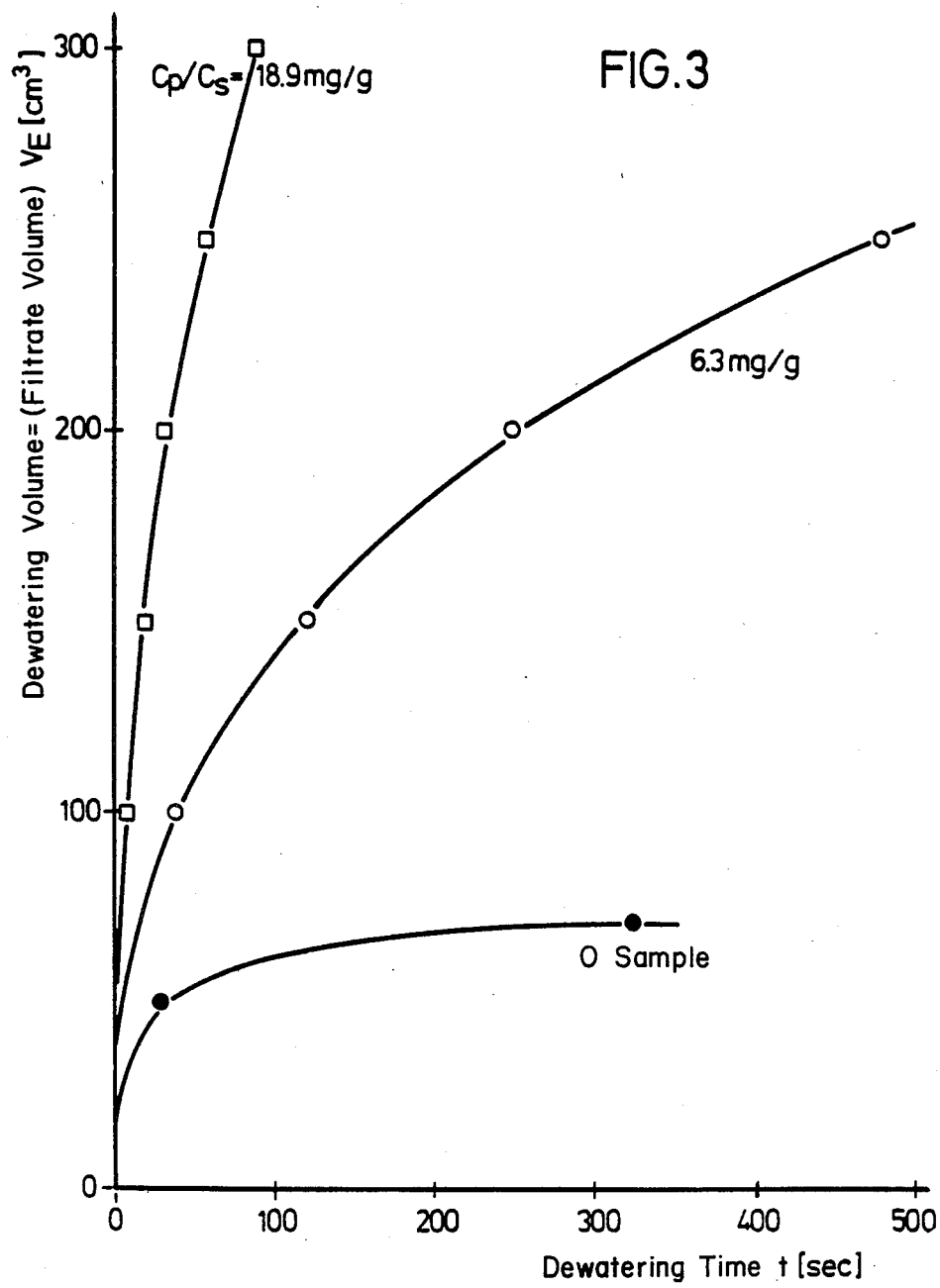

Three Examples of the invention are presented below and are described in detail. In the drawing, FIG. 1 shows a control apparatus for a sludge dewatering machine (e.g. a pressure belt filter, a decanter or a chamber filter press), FIG. 2 shows the dependence of the measured drop in pressure $\Delta p$ [mbar] on the specific metering of assistant $C_p/C_s$ [mg/g] in a typical digested sludge suspension, and FIG. 3 shows the dependence of the filtrate volume $V_E$ [cm$^3$] on the dewatering time t [sec] for various metered amounts of assistant according to FIG. 2.

FIG. 1 is a diagram of the arrangement of a control apparatus in a conventional sludge dewatering machine 1, with a filtrate outflow 2 and a sludge discharge 3. By means of a motor 4 connected via a line 5 to a control unit 14, the throughput can be adapted, for example via the filter speed, to the specific sludge conditions in a sludge feed 6.

The dispersion to be dewatered passes through a feed line 7 to a sludge pump 8 which, by means of a drive motor 9 and a line 10 to a control unit, permits variable throughput.

The mass flow is determined downstream from the sludge pump 8, by means of a density measurement 11 and a flow rate measurement 12. Both measuring instruments 11 and 12 are connected to the control unit 14 via a line 13. The line 13 also connects the flow rate measurement to a control unit 15.

The flocculant is metered via a pump 16 which has a variable-speed motor 17 and is located in a flocculant line 18. Rapid mixing of the flocculant and the dispersion is effected in a mixing element 19. The motor 17 is connected to the control unit 14 via a line 20.

Measurement of the pressure drop in sludge feed 6 is carried out upstream from mixing element 19 by means of pressure gage 21, and downstream from the said mixing element by means of pressure gage 22. Both pressure gages 21 and 22 are connected to the control unit 14 via lines 23. The pressure gages 21 and 22 can be located either directly in the sludge feed line 6, as in FIG. 1, or in appropriate bypass lines.

Accordingly, the mode of operation of the control unit 14, which is responsible for metering the flocculant, is dependent on the densimeter 11, the flowmeter 12 and the ratio of the values measured by the two pressure gages 21 and 22; the motors 4 and 17 are influenced. The control unit 15 is provided for the throughput of the dispersion, and is connected via the line 13 to the flowmeter 12 and to an apparatus 24 for measuring the sludge level or to a cake thickness detector 25.

The essential feature is that the standardized pressure drop in the flowing dispersion, determined from the two pressure measurements 21 and 22, is used as a control input for the flocculant control loop. The addition of flocculant is optimized by virtue of the fact that the standardized pressure drop is adjusted to the minimum value or, if desired, to a predetermined value, in particular by virtue of the fact that the said pressure drop settles to this value as a result of iterative steps. The predetermined ideal value can also be adapted, via the mass flow measurements, to fluctuations in the sludge feed.

FIG. 2 illustrates a typical result of a pressure measurement carried out, in accordance with the invention, two meters downstream from the point at which a cationic assistant was metered. The pressure drop was measured over a distance of one meter in a pipeline having an internal diameter of 3 mm, at a throughput of 100 $cm^3$/min. The dispersion used was a municipal digested sludge containing 19 $g/dm^3$ of dry solid matter. The assistant was metered from a stock solution of 8 $g/dm^3$, the amount metered being varied in the range from 6.3 to 27.4 mg of assistant per g of substrate. The ratios are typical for a novel pressure measurement in a bypass of a sludge feed line.

For small metered amounts, i.e. from 6.3 to 12.6 mg/g, the pressure drop initially increases compared with the reference value for the unflocculated system, and then falls abruptly below the reference value when amounts greater than 18.9 mg/g are metered. When metering of the assistant is complete, the pressure drop returns to the initial value. If samples of the flocculated sludge are taken after various amounts have been metered and are introduced into glass cylinders, it is found, surprisingly, that there is a correlation between the abrupt decrease in the pressure drop and the appearance of the first readily visible macroflocs.

This finding is confirmed by the corresponding dewatering curves for samples taken when amounts of 6.3 and 18.9 mg/g had been metered (FIG. 3).

Pronounced acceleration of the dewatering results even when a smaller amount is metered. A very substantial increase can be achieved when the critical metering of 18.9 mg/g appearing in FIG. 2 is exceeded. A further increase in the amount metered results only in slight improvements in the dewatering behavior.

We claim:

1. A method for rapid in situ estimation of the degree of dispersion in a flowing two-phase system, in particular for determining optimum metering of a dispersant or flocculant in a concentrated dispersion, wherein assignment of the degree of dispersion is effected by measuring the pressure drop experienced by a flowing dispersion along a defined length during tubular flow.

2. A method as claimed in claim 1, wherein the measurement is carried out downstream from a point at which an assistant is metered.

3. A method as claimed in claim 2, wherein a second, similar measurement of the pressure drop is carried out upstream from the point at which the assistant is metered, and the measured value obtained is used for standardizing the measured value obtained downstream.

4. A method as claimed in claim 2, wherein the measured value is used as a control input for a flocculant control loop in an apparatus for solid/liquid separation, in particular a dewatering machine with one or more control loops for adaptation to sludges or dispersions with fluctuating dewatering properties, such as a flocculant control loop and/or a throughput control loop or a filter speed control loop in the case of a pressure belt filter. Drawing.

* * * * *